United States Patent [19]

Fujita-Yamaguchi et al.

[11] Patent Number: 4,962,155

[45] Date of Patent: Oct. 9, 1990

[54] METHODS AND COMPOSITIONS FOR ACTIVATING THE HUMAN INSULIN RECEPTOR KINASE

[75] Inventors: Yoko Fujita-Yamaguchi, Glendora, Calif.; Jay M. McDonald; David B. Sacks, both of St. Louis, Mo.

[73] Assignees: City of Hope, Duarte, Calif.; Washington University, St. Louis, Mo.

[21] Appl. No.: 129,307

[22] Filed: Dec. 7, 1987

[51] Int. Cl.$^5$ .................... A61K 37/02; A61K 37/26; C08H 1/00; C08L 89/00
[52] U.S. Cl. ................................ 525/54.1; 530/303; 530/395; 530/807; 530/815
[58] Field of Search ............... 525/54.1; 530/303, 345, 530/395, 807, 815

[56] References Cited

U.S. PATENT DOCUMENTS

| | | | |
|---|---|---|---|
| 3,847,155 | 11/1974 | Bernaola | 128/334 |
| 4,411,832 | 10/1983 | Cuatrecasas et al. | 530/362 |
| 4,761,371 | 8/1988 | Bell et al. | 935/56 |

Primary Examiner—Nathan M. Nutter
Attorney, Agent, or Firm—Edward S. Irons

[57] ABSTRACT

A method of activating human insulin receptor kinase and a method of reactivating human receptor kinase which has lost some, but not all, of its kinase activity, comprising reacting human insulin receptor with at least one basic protein.

11 Claims, 5 Drawing Sheets

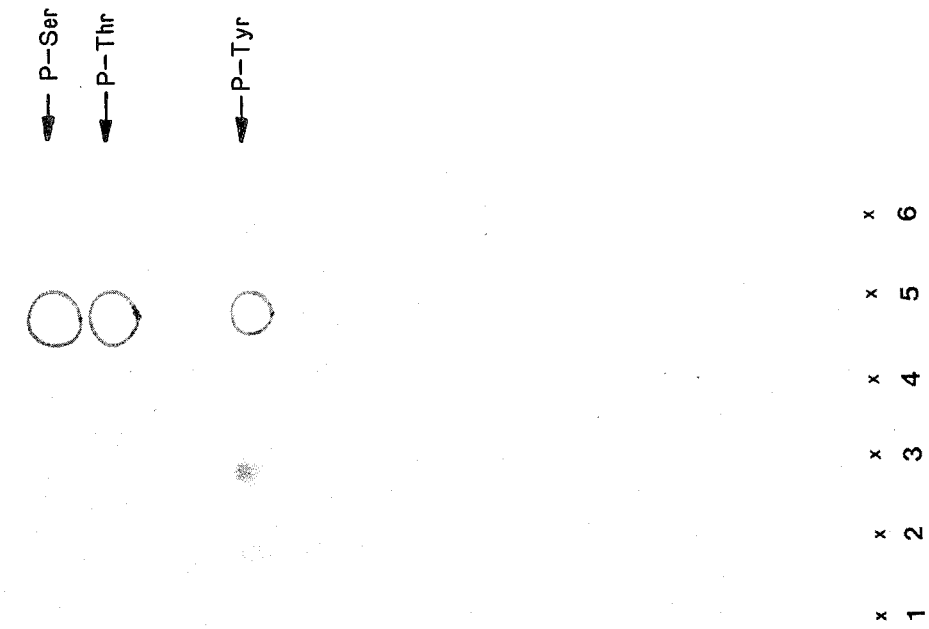
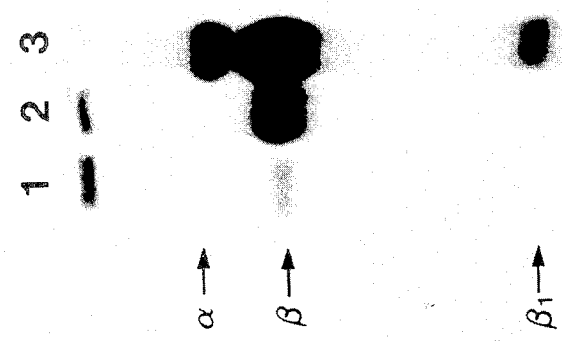
FIG. 4A
FIG. 4B

METHODS AND COMPOSITIONS FOR ACTIVATING THE HUMAN INSULIN RECEPTOR KINASE

BACKGROUND OF THE INVENTION

This invention relates to methods and compositions for activating or stimulating the human insulin receptor kinase. This invention also relates to methods and compositions for restoring the kinase activity of human insulin receptor which has lost some of its activity, and for stimulating kinase activity in human insulin receptor which does not possess insulin-sensitive kinase activity.

Regulation of cellular metabolism and growth by insulin is a result of a series of events initiated by the interaction of insulin with specific cell surface receptors. The molecular mechanism of insulin action is not well understood especially with respect to the events following the binding of the receptor which ultimately lead to the cellular responses.

The insulin receptor is an integral transmembrane glycoprotein ($M_r \approx 300,000$) comprising two $\alpha$ subunits ($M_r \approx 125,000$) and two $\beta$ subunits ($M_r \approx 95,000$) in a $\beta$-$\alpha$-$\alpha$-$\beta$ form linked by disulphide bonds. The $\alpha$ subunit and the amino-terminal portion of the $\beta$ subunit are on the extracellular side of a target cell's membrane, and the carboxyl-terminal two-thirds of the $\beta$ subunit is located in the target cell's cytoplasm.

The $\alpha$-subunit is responsible for insulin binding. The binding of insulin to the extracellular $\alpha$ domain of the receptor results in activation of a kinase which is coded in the cytoplasmic domain of the $\beta$ subunit. It is now known that this kinase is a tyrosine-specific protein kinase, Ullrich, A., et al., *Nature* 313:756 (1985); Ebina, Y., et al., *Cell* 40:747 (1985); and Gammeltoft, S., et al., *Biochem J.* 235:1 (1986). The tyrosine-specific protein kinase phosphorylates tyrosine residues on the $\beta$ subunit, a process known as autophosphorylation, as well as other substrates. Thus, in intact cells, insulin stimulates the phosphorylation of its own receptor $\beta$ subunit.

Studies of insulin resistance have mainly focused on insulin binding, however abnormalities in insulin binding account for only a part of the alteration of insulin's action. In such an instance, postbinding receptor abnormalities may also exist.

Tyrosine protein kinase activity of the insulin receptor is now thought, to mediate some or all of insulin actions. Gammeltoft, S., et al., *Biochem J.* 235:1 (1986).

Inhibitors or activators of tyrosine-specific kinases can be useful not only in the biochemical characterization of these enzymes, but also for understanding the physiological roles in vivo of these enzymes. Inhibitors thus far reported include small compounds such as amiloride, Davis, R. J., et al., *J. Biol. Chem.* 260:2543 (1985); genistein, Akiyama, T., et al., *J. Biol. Chem.* 262:5592 (1987), and quercetin, Graziani Y., et al., *Biochim. Biophys. Acta.* 714:415 (1981), and some types of tyrosine-containing synthetic polymers, Sahal, D., et al., *Arch. Biochem. Biophys* (1988) (in press). Insulin and its mimickers such as dithiothreitol, vanadate (sodium orthovanadate), $H_2O_2$ (hydrogen peroxide), anti-insulin receptor antibodies, and concanavalin A have been shown to activate the insulin receptor kinase, Fujita-Yamaguchi Y., et al., *Proc Natl. Acad. Sci., USA* 82:6095 (1985); Tamura, S., et al., *J. Biol Chem.* 259:6650 (1984); and Roth, R. A., et al., *Biochem. Biophys. Res. Commun.* 115:245 (1983). Inactivation of the insulin receptor kinase during and after purification has posed serious problems. Kathuria, S., et al., *Proc. Natl. Acad. Sci., USA* 83:8570 (1986), report that the intact 90-KDa $\beta$ subunit has full kinase activity, while degraded forms such as an 88-KDa form exhibit little kinase activity. This inactivation of the kinase appears to arise from a conformational change in the 90-KDa form. When aged, the intact insulin receptor kinase may become relatively inactive, showing low or no insulin-stimulatory activity. This process is accelerated when the receptor is kept at 4° C. or 37° C. Freezing the receptor at −70° C. in the presence of 10% glycerol significantly improves the stability of kinase activity, however, a decrease in activity accompanied with a loss of insulin stimulation has been observed.

Studies of insulin action have also focused on calmodulin, a ubiquitous $Ca^{+2}$ binding regulatory protein and on basic proteins. For example, Graves, C. B., et al., *J.Biol.Chem.* 261:10429 (1986) reported, using solubilized enriched insulin receptor preparations from adipocytes, that calmodulin enhances insulin-stimulated phosphorylation of the $\beta$ subunit of the insulin receptor and histone H2b. Laurino, J. P., et al. report (submitted for publication to *Eur. J. Biochem.*) that in rat adipocyte insulin reactor preparations, exogenous proteins such as poly L-lysine, histone Hf2b, and protamine sulfate are required to obtain the insulin receptor catalyzed phosphorylation of an exogenous substrate calmodulin. Sacks, D. B., et al. *J. Biol. Chem.* 1988 (in press) further report that in rat hepatocyte insulin reactor preparations, exogenous basic proteins such as poly L-lysine, histone Hf2b, and protamine sulfate are required to obtain insulin-stimulated phosphorylation of calmodulin and that such proteins in the absence of insulin appeared to stimulate the phosphorylation of both the $\beta$ subunit of the insulin receptor and calmodulin. It was also reported that other basic proteins such as poly ornithine and poly arginine are effective to stimulate the phosphorylation of the $\beta$ subunit of the insulin receptor.

SUMMARY OF THE INVENTION

In general, the invention features a method of activating or stimulating human insulin receptor kinase, comprising reacting human insulin receptor with at least one basic protein. In preferred embodiments, the basic proteins are poly L-lysine and poly L-ornithine.

The invention also features a method of reactivating human insulin receptor kinase which has lost some, but not all, of its kinase activity, comprising reacting human insulin receptor with a basic protein. In preferred embodiments, the basic protein is poly L-lysine.

The invention further features a method of activating or stimulating human insulin receptor without insulin-sensitive kinase activity, comprising reacting human insulin with a basic protein. In preferred embodiments, the basic protein is poly L-lysine.

Other advantages and features of the invention will be apparent from the following description of the preferred embodiments thereof, and from the claims.

DESCRIPTION OF THE DRAWINGS

FIG. 4A shows a photograph of an autoradiogram from a silver stained SDS polyacrylaminde gel containing phosphorylated insulin receptor that was preincubated with either insulin or poly L-lysine.

FIG. 4B is a photograph of the results of phosphoamino acid analysis by paper electrophoresis of the $\beta$ and $\alpha$ subunits of insulin receptor preparations phosphorylated in the presence of insulin or poly L-lysine.

FIG. 6A and 6B show the results from one receptor preparation which shows insulin stimulated kinase activity; FIG. 6C shows the results from receptor preparations which had lost insulin-dependent kinase activity. Kinase activity was measured at varying concentrations of the src-related peptide substrate: basal activity (o), insulin-stimulated kinase activity (●), and poly L-lysine-stimulated kinase activity (x).

DESCRIPTION OF THE PREFERRED EMBODIMENT

Figure 1:
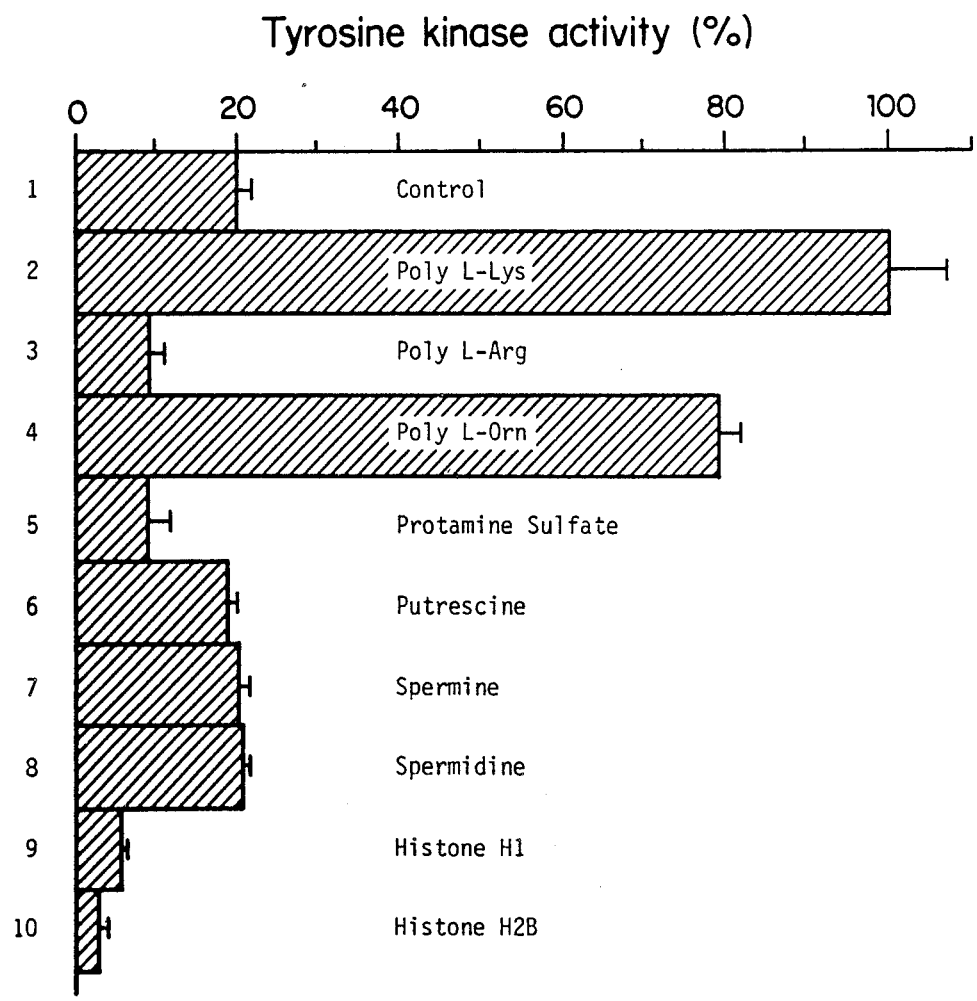
FIG. 1 shows the tyrosine kinase activity of purified insulin receptor after the receptor was preincubated with a variety of basic proteins or polyamines and then assayed for kinase activity.

According to the methods of the present invention it has been found that some basic proteins activate the human insulin receptor kinase and reactivate human insulin receptor which has lost most, but not all, of its kinase activity. It has further been found that at least one basic protein can stimulate kinase activity of receptor preparations which do not possess insulin-sensitive kinase activity.

The activation of insulin receptor which possesses normal tyrosine-specific kinase activity is much greater than the activation of the insulin receptor kinase caused by insulin, and appears to be independent of insulin activation. An activation of the kinase which is independent of that caused by insulin is important because some types of diabetes exhibit insulin-resistant kinase impairment. Grigorescu, F., et al., J. Biol. Chem. 259:15003 (1984); Grunberger, G., et al., Science 223:932 (1984) and J. Clin. Endocrinol. Metab. 59:1152 (1984); Kadowaki, T., et al., J. Biol.. Chem. 259:14208 (1984); and Le Marchand-Brustel, Y., et al., Nature 315:676 (1985).

Methods

Tyrosine-specific protein kinase activity of the insulin receptor was studied using the receptor purified from human placentas. The substrate used is a synthetic peptide (src-related peptide) which resembles the amino acid sequence around the site of phosphorylation of the tyrosine residue in the Rous sarcoma virus transforming protein, pp60$^{src}$, with the sequence (Arg-Arg-Leu-Ile-Glu-Asp-Ala-Glu-Tyr-Ala-Ala-Gly), Casnellie, J. E., et al., Proc. Natl. Acad. Sci. USA 79:282 (1982).

The insulin receptor was purified from Triton X-100 solubilized human placental membranes by sequential affinity chromatography on wheat germ agglutinin and insulin-Sepharose as described by Fujita-Yamaguchi, Y., et al., J. Biol. Chem. 258:5045 (1983).

Phosphorylation of Exogenous Substrate (Kinase Assay)

Phosphorylation assays which measure insulin receptor kinase activity were carried out using the src-related peptide identified above as an exogenous substrate. The purified insulin receptor (0.1 μg) was preincubated with insulin or a basic protein or polyamine at 25° C. for 1 hour. The phosphorylation assays were carried out at 25° C. for 40 minutes in 30 ul of 50 mM Tris-HCl buffer (pH 7.4) containing 1 mM of the src-related peptide, 2 mM MnCl$_2$, 15 mM MgCl$_2$, 0.1% Triton X-100, and 40 μM [γ-$^{32}$]ATP (12,000 cpm/pmole). The reaction was terminated by adding 50 μl of 5% trichloroacetic acid (TCA) and 20 μl of bovine serum albumin (BSA) (10 mg/ml), the resulting solution was then incubated at 0° C. for 30 minutes, and the proteins were precipitated by centrifugation. Aliquots (35 μl) of the resulting supernatant were spotted on phosphocellulose paper (Whatman, P-81). The papers were extensively washed in 75 mM phosphoric acid. Duplicates of the papers were prepared from each reaction mixture and $^{32}$P incorporated into the src-related peptide was counted using a liquid scintillation counter.

Phosphorylation of the β Subunit

The β subunit of the purified receptor was phosphorylated in the same manner as described above for the exogenous substrate phosphorylation. The reaction was terminated by adding 3-times concentrated Laemmli's sample buffer followed by boiling for 5 minutes. SDS-polyacrylamide gel electrophoresis was then performed under reducing conditions as described by Laemmli, U. K., Nature 227:680 (1970). The gels were stained with silver, dried, and autoradiographed.

EXAMPLE 1

The tyrosine-specific protein kinase activity of purified insulin receptor was assayed by measuring $^{32}$P incorporation into src-related peptide after the receptor was preincubated with a variety of basic proteins or polyamines according to the above-described protocol. The specific basic proteins or polyamines used in these assays were poly L-lysine, poly L-arginine, poly L-ornithine, protamine sulfate, putrescine, spermine, spermidine, histone H1, and histone H2B.

FIG. 1 shows the results of the effects that these basic proteins had on insulin receptor kinase activity. The rate of kinase activity of each sample is expressed as the percentage of the maximal activity achieved in the presence of 1 μM of poly L-lysine. Shown are the average and standard deviation of three independent experiments using the same insulin receptor preparation.

As seen in FIG. 1, at a concentration of 1 μM, poly L-lysine and poly L-ornithine activated the insulin receptor kinase approximately 5 fold and approximately 4 fold, respectively, over the control. The rest of the basic proteins showed either no positive effect or an inhibitory effect.

EXAMPLE 2

Figure 2:
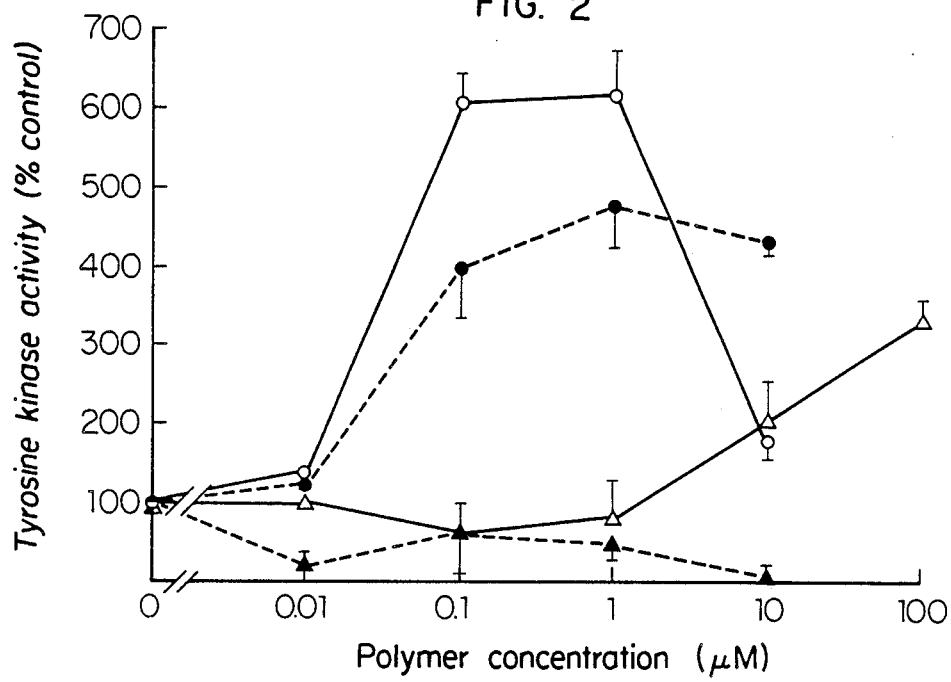
FIG. 2 shows dose response curves for different concentrations of four proteins which exhibit some stimulatory or inhibitory effects on insulin receptor kinase activity: poly L-lysine (o); poly L-ornithine (●); protamine sulfate (Δ); and poly L-arginine (▲).

Dose responses for four proteins which exhibited some stimulatory (poly L-lysine, poly L-ornithine) or inhibitory effects (protamine sulfate, poly L-arginine) in Example 1 are shown in FIG. 2.

Approximately 0.1 ug of purified insulin receptor was preincubated with different concentrations of poly L-lysine (o), poly L-orinithine (●), protamine sulfate (Δ), or poly L-arginine (▲). The tyrosine kinase activity of the insulin receptor was assayed by measuring the incorporation of $^{32}P$ into the src-related peptide substrate according to the above-described phosphorylation assay method. The rate of kinase activity is expressed as the percentage of the basal kinase activity the activity of purified insulin receptor preincubated in the Tris HCl buffer containing neither basic proteins nor insulin.

As seen in FIG. 2, poly L-Lysine stimulated kinase activity at concentrations of about 0.1 $\mu M$ to about 1 $\mu M$. Poly L-ornithine was stimulatory at concentrations of about 0.1 to about 10 $\mu M$. Protamine sulfate exhibited stimulatory effects only at higher concentrations, approximately two-fold at 10 $\mu M$ and approximately 3.5 fold at 100 $\mu M$. By contrast, poly L-arginine inhibited the kinase activity of the receptor at any of the concentrations examined.

EXAMPLE 3

The effects of poly L-lysine itself or both poly L-lysine and insulin on insulin receptor kinase activity were determined as follows. Purified insulin receptor (approximately 0.1 ug) was preincubated at 25° C. for 1 hour with various concentrations of poly L-lysine in the absence or presence of 1 $\mu M$ insulin in 20 $\mu l$ of 50 mM Tris HCl buffer (pH 7.4) containing 0.1% Triton X-100. Tyrosine kinase activity of the receptor was assayed by measuring $^{32}P$ incorporation into the src-related peptide as described above.

Figure 3A:
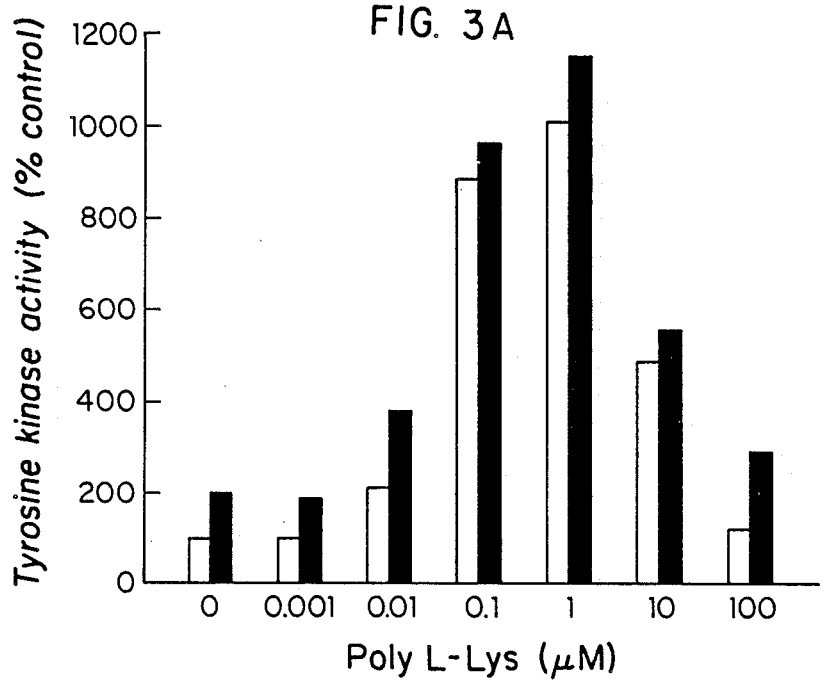
FIG. 3A shows the effects of different concentrations of poly L-lysine on insulin receptor kinase activity after purified insulin receptor was preincubated in the absence (□) and presence (■) of 1 μM insulin and then assayed for kinase activity.

The kinase activities resulting from these experiments are shown in FIG. 3A for both insulin receptor incubated in the absence (□) or presence (■) of insulin. The rate of kinase activity is expressed as the percentage of the basal kinase activity, that is, the activity of the purified insulin receptor preincubated in Tris-HCl buffer containing neither poly L-lysine nor insulin. The average results of two independent experiments using the same receptor preparation are shown.

The results of FIG. 3A show that the stimulative effects of insulin and poly L-lysine are additive and independent of each other insulin can activate kinase to the same degree as the control (0 $\mu M$ poly L-lysine) in the presence of 100 $\mu M$ poly L-lysine, where the stimulative effect of poly L-lysine can no longer be seen. Moreover, the kinase activation by poly L-lysine at optimum concentrations is much greater than the kinase activation by insulin. In sum, poly L-lysine stimulation is much greater than insulin stimulation and the effects of insulin and poly L-lysine are additive.

The effects of poly L-lysine alone or poly L-lysine and insulin together on the autophosphorylation of the insulin receptor $\beta$ subunit were determined. After the kinase reaction was terminated by adding TCA and BSA as described in the above procedures, the proteins containing the insulin receptor were precipitated by centrifugation. The precipitated proteins were then subjected to SDS polyacrylamide gel electrophoresis (7.5% gel) under reducing conditions. The gels were stained with silver, dried, and autoradiographed for 30 hours using a Kodak XAR-5 film and an intensifying screen.

Figure 3B:
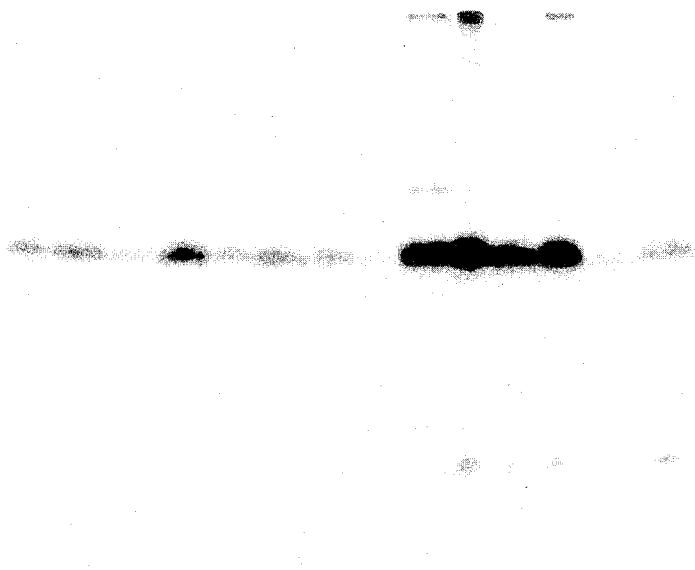
FIG. 3B shows a photograph of an autoradiogram of a silver stained sodium dodecylsulfate (SDS) polyacrylamide gel. The assays contained insulin receptor preincubated with different concentrations of poly L-lysine in the presence and absence of 1 μM insulin and then phosphorylated.

One of the autoradiograms derived from the two experiments (poly L-lysine in the presence and absence of insulin) described with reference to FIG. 3A is shown in FIG. 3B. Lanes 5, 7, 9, 11, and 13 contain insulin receptor preparation preincubated with 0.001, 0.01, 0.1, 1, and 10 $\mu M$ poly L-lysine, respectively. Lanes 6, 8, 10, 12, and 14 contain insulin receptor preparation preincubated with 0.001, 0.01, 0.1, 1, and 10 $\mu M$ poly L-lysine, respectively, but in the Presence of 1 $\mu M$ insulin. Lanes 1-4 are controls with lanes 1 and 3 representing basal autophosphorylation (insulin receptor incubated with only Tris-HCl buffer) and lanes 2 and 4 representing insulin-stimulated autophosphorylation.

Comparison of the autoradiogram results in which the same concentration of poly L-lysine was used without and with the addition of 1 $\mu M$ insulin (lanes 5 and 6 (0.001 $\mu M$), lanes 7 and 8 (0.01 $\mu M$), lanes 9 and 10 (0.1 $\mu M$), lanes 11 and 12 (1 $\mu M$) and lanes 13 and 14 (10 $\mu M$), respectively) shows, as with the results of FIG. 3A (with the exception of lane 8), that poly L-lysine stimulation is greater than that of insulin. That is, the autoradiogram shows noticeably more phosphorylation in lanes 6, 10, 12, and 14 than that in lanes 5, 9, 11, and 13. The intensity of the $\beta$ subunit phosphorylation in lane 8 was lower than expected with respect to the kinase activity assay performed from which the lane 8 material was derived. This result is likely an artifact due to misloading the lane 8 sample for the electrophoresis. In sum, the results shown in FIG. 3A correlate with the FIG. 3B results, that is, poly L-lysine stimulation of the insulin receptor tyrosine kinase is greater than insulin stimulation of the kinase, and their effects are additive.

EXAMPLE 4

Phosphorylation of insulin receptor subunits in the presence or absence of poly L-lysine was carried out by preincubating approximately 0.4 $\mu g$ of purified insulin receptor with Tris HCl buffer, 1 $\mu M$ insulin, or 0.25 $\mu M$ poly L-lysine. The insulin receptor was then phosphorylated according to the procedures described above. After the phosphorylation, the receptors were analyzed by SDS polyacrylamide gel electrophoresis (10% gel) under non-reducing conditions. The gel was dried and autoradiographed for 45 minutes at −70° C. by exposing the gel to a Kodak XAR-5 film with an intensifying screen.

A photograph of the resulting autoradiogram gel is shown in FIG. 4A. Insulin receptor preincubated with Tris-HCl buffer (basal $\beta$ subunit autophosphorylation) is in lane 1, receptor preincubated with insulin (insulin-stimulated $\beta$ subunit autophosphorylation) is in lane 2, and receptor preincubated with poly L-lysine (poly L-lysine stimulated phosphorylation) is in lane 3. The results in lane 3 show poly L-lysine also stimulates phosphorylation of $\alpha$ and $\beta_1$ subunits in addition to the $\beta$ subunit. phosphoamino acids of the $\beta$ and $\alpha$ subunits of the insulin receptor treated with insulin or poly L-lysine were analyzed by cutting out the bands shown in FIG. 4A, washing the gel pieces, eluting the subunit peptides by trypsin digestion as described by Fujita-Yamagachi, Y., *J. Biol.. Chem* 254:1206 (1984), and hydrolyzing the peptides in 2N HCl for 2 hours at 110° C. The materials were then analyzed by paper electrophoresis (pH 3.5, 2000 V, 1 hour) and autoradiography.

The results of such analysis are shown in FIG. 4B. Lanes 1–4 of FIG. 4B contain amounts of hydrolysates equal to 50% of the starting materials from the FIG. 4A gel. Lane 1 (760 cpm) represents β subunit basal phosphorylation; lane 2 (1600 cpm) represents insulin stimulated β subunit phosphorylation; lanes 3 (4400 cpm) and 4 (1000 cpm) represent poly L-lysine-stimulated phosphorylation of the β and α subunits, respectively. Lane 6 (1700 cpm) contains 20% of the original material of poly L-lysine-stimulated β subunit phosphorylation (40% of the amount applied to lane 3). Lane 5 shows ninhydrin-stained phosphoamino acids, from top, phosphoserine, phosphothreonine, and phosphotyrosine. Other radioactive samples were electrophoresed together with these three phosphoamino acids. Ninhydrin spots for those are not shown. X indicates the origin of the samples.

The kinase activity with which the present invention is concerned is denoted tyrosine-specific kinase since the substrate, src-related peptide, contains only tyrosine as a potential phosphorylation site. As seen in FIG. 4B, when β and α subunits phosphorylated by either insulin or poly L-lysine were analyzed for phosphoamino acid composition as described above, tyrosine was found to be a major amino acid whose phosphorylation was stimulated by insulin (lane 2) or by poly L-lysine (lanes 3 and 4). A significant amount of phosphoserine was observed, which may have been due to contamination of the receptor preparation used. Lane 6 shows the relative intensity of the two $^{32}$P-labeled phosphoamino acids when 40% of the same sample applied on lane 3 was electrophoresed. The ratio of P-Ser/P-Tyr in lane 6 corresponds roughly to that of lane 2, which indicates that insulin and poly L-lysine stimulate phosphorylation of both amino acids in a similar manner.

EXAMPLE 5

The possibility that poly L-lysine may be able to activate the insulin receptor kinase whose activity has been reduced and can no longer be stimulated by insulin was investigated.

Table I below summarizes the kinase and autophosphorylation activity of purified receptor preparations which had been stored at −70° C. for various periods of time.

TABLE I

Effects of poly L-Lysine (PLL) and insulin on kinase activity of highly purified insulin receptor preparations after storage at 70° C.

| Insulin receptor preparations | Period of storage at −70° C. | Kinase activity pmol/min | (Preincubated with) |
|---|---|---|---|
| A | 36 Mo. | 0 | Insulin |
|   |   | 0 | .* |
|   |   | 0.002 | PLL |
| B | 28 Mo. | 0.026 | Insulin |
|   |   | 0.026 | .* |
|   |   | 0.174 | PLL |
| C | 15 Mo. | 0.042 | Insulin |
|   |   | 0.016 | .* |
|   |   | 0.229 | PLL |
| D | 3 Mo. | 0.364 | Insulin |
|   |   | 0.109 | .* |
|   |   | 2.30 | PLL |
| E | <3 Days | 0.156 | Insulin |
|   |   | 0.018 | .* |

TABLE I-continued

Effects of poly L-Lysine (PLL) and insulin on kinase activity of highly purified insulin receptor preparations after storage at 70° C.

| Insulin receptor preparations | Period of storage at −70° C. | Kinase activity pmol/min | (Preincubated with) |
|---|---|---|---|
|   |   | 1.13 | PLL |

*Basal activity.

As shown in Table I, the kinase activity of receptor preparations A–E ranging from preparation stored for as long as 36 months to fresh preparation (<3 days) were preincubated with 1 μM insulin, 0.24 μM poly L-lysine, or nothing (basal activity). During storage at −70° C., basal kinase activity is gradually lost, and aged receptor kinase eventually loses its insulin dependency.

Further, poly L-lysine can activate certain old insulin receptor preparations which (1) have lost both basal and insulin-dependent kinase activities, as seen in 36 month old preparation A, and (2) have just lost insulin dependent activity, as seen in 28 month old preparation B. Older preparations showed no kinase activity eve after poly L-lysine treatment (data not shown), which indicates that poly L-lysine can activate insulin receptor kinase which is partially, but not completely, inactivated. The degree of activation by poly L-lysine as compared to basal activity varied from 6 to 60-fold, whereas the relative activation by poly L-lysine as compared to insulin-dependent kinase activity was always approximately 10-fold.

Figure 5:
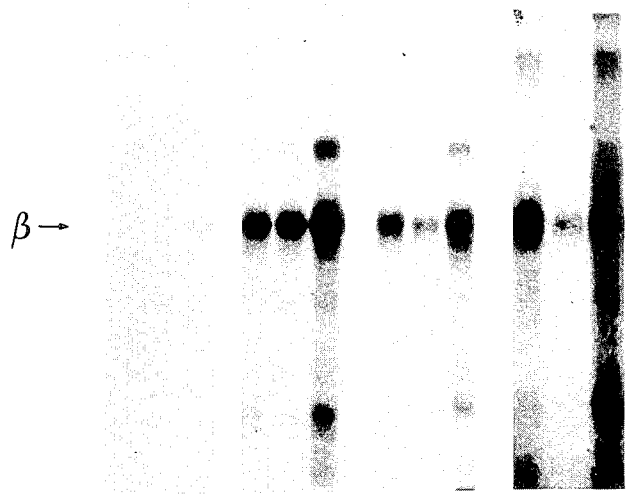
FIG. 5 shows a photograph of an autoradiographed silver stained SDS polyacrylamide gel demonstrating the effects of poly L-lysine on insulin receptor autophosphorylation. Freshly Prepared and stored insulin receptor preparations were incubated with 1 μM insulin (lanes 1, 4, 7 and 10), incubated with nothing (lanes 2, 5, 8 and 11), or incubated with 0.24 μM poly L-lysine (lanes 3, 6, 9 and 12), and phosphorylated.

The effects of poly L-lysine on insulin receptor autophosphorylation are shown in FIG. 5. Freshly prepared Purified insulin receptor (less than three days old) (lanes 10–12) and purified receptor preparations stored at −70° C. for 36 months (lanes 1–3), 28 months (lanes 4–6), and 15 months (lanes 7–9) were incubated with 1 μM insulin (lanes 1, 4, 7, and 10), nothing (lanes 2, 5, 8, and 11), or 0.24 μM poly L-lysine (lanes 3, 6, 9, and 12). Lanes 1–3, 4–6, 7–9, and 10–12 further correspond to insulin receptor preparations A, B, C, and E in Table I, respectively. The results of preparation D are shown in FIG. 4A. Phosphorylation assays were then carried out as described in the above. The various receptors were analyzed by SDS polyacrylamide gel electrophoresis (7.5% gel) under reducing conditions. The gel was stained with silver, dried, and autoradiographed. The results of the autophosphorylation reactions carried out agreed with those of kinase activity in Table I.

EXAMPLE 6

Figure 6A:
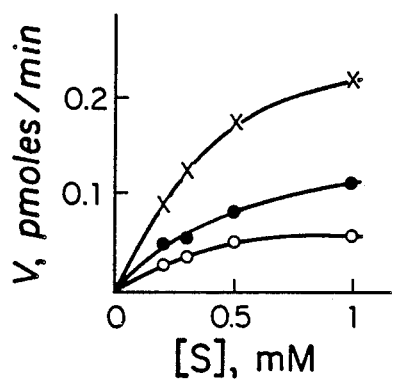
FIGS. 6A, 6B and 6C are graphs showing kinetic analyses of the insulin receptor treated with 0.24 μM poly L-lysine or 1 μM insulin.

Kinetic analyses on the insulin receptor kinase were performed with or without 0.24 μM poly-L-lysine treatment. The results of these studies are shown in FIGS. 6A, 6B, and 6C.

Approximately 0.1 μg of purified insulin receptor was preincubated with 1 μM insulin or 0.24 μM poly L-lysine at 25° C. for 1 hour as described above. The kinase activity of the receptor was then measured at varying concentrations of the src-related peptide substrate. In FIGS. 6A–6C basal activity is indicated by (o), insulin-stimulated kinase activity is indicated by (●), and poly L-lysine-stimulated stimulated kinase activity is indicated by (x). FIGS. 6A and 6B resulted from fresher insulin receptor preparation which showed insulin-stimulated activity; FIG. 6C shows the results from another receptor preparation which had lost insulin-dependent kinase activity.

Figure 6B:
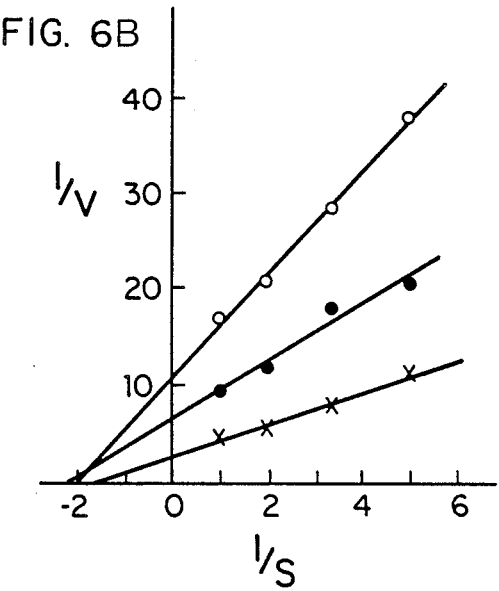
Figure 6C:
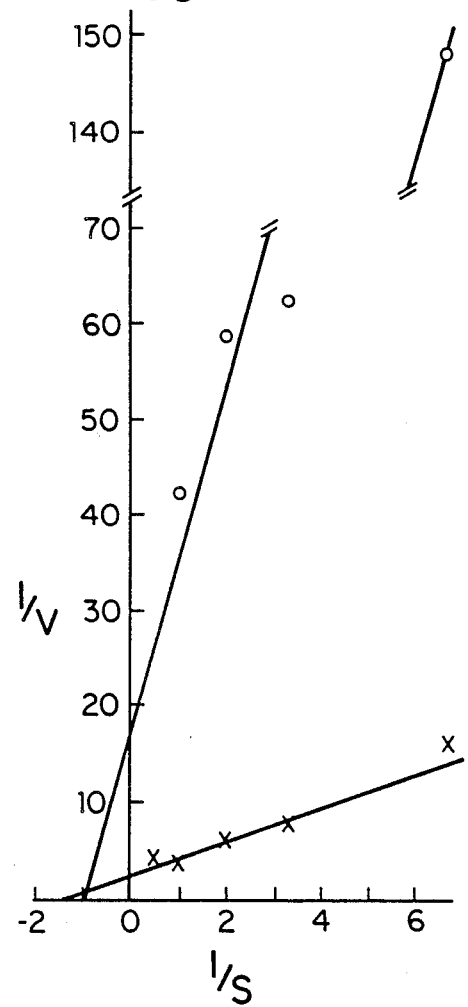

The Lineweaver-Burk plots shown in FIGS. 6B and 6C show that poly L-lysine activates the insulin receptor kinase by increasing $V_{max}$ without significantly changing $K_M$.

It has been previously reported by Fujita-Yamaguchi, Y., et al., *Proc. Natl. Acad. Sci. USA* 82:6095 (1985) that dithiothreitol (DTT) activates the insulin receptor kinase. The effect of DTT on kinase activity was compared with that of insulin (INS) and poly L-lysine (PLL). The results are summarized in Table II below.

TABLE II

Effects of Poly L-lysine, Insulin, and Dithiothreitol on Kinase Activity of Highly Purified Insulin Receptor

| Preincubation With | | | Kinase Activity | |
| --- | --- | --- | --- | --- |
| INS | PLL | DTT | pmol/min | −fold |
| — | — | — | 0.006 | 1 |
| 1 µM | — | — | 0.016 | 2.7 |
| — | 0.24 µM | — | 0.234 | 39 |
| — | — | 0.1 mM | 0.059 | 9.8 |
| — | — | 0.5 mM | 0.083 | 13.8 |
| — | 0.24 µM | 0.1 mM | 0.250 | 41.7 |
| — | 0.24 µM | 0.5 mM | 0.497 | 82.8 |

As seen in Table II, 1 µM insulin and 0.1 mM DTT activated the kinase approximately 3-fold and approximately 10-fold, respectively. Kinase activation by 0.24 µM poly L-lysine and 0.1 mM DTT was approximately 40-fold, which is much greater than the activation due to either insulin or DTT.

The above examples show that poly L-lysine and poly L-ornithine are able to stimulate the insulin receptor kinase at concentrations of about 0.1–1.0 µM. Both stimulated tyrosine-specific kinase activity of the insulin receptor by about 5 to about 10 fold. Protamine sulfate also showed significant stimulative effect but at a much larger concentration of 100 µM. Such compounds could therefore effectively be used to treat certain forms of human diabetes.

The above examples also show that poly L-lysine activates the insulin receptor kinase by increasing $V_{max}$ without significantly changing $K_M$.

Poly L-lysine is also able to restore the kinase activity of insulin receptor preparation that have lost some, but not all, kinase activity and of receptor preparations without insulin-sensitive kinase activity.

What is claimed is:

1. A method of activating human insulin receptor kinase, comprising:
    reacting human insulin receptor with poly L-lysine, poly L-ornithine, or protamine sulfate.
2. The method of claim 1 wherein said basic protein is poly L-lysine.
3. The method of claim 1 wherein said basic protein is poly L-ornithine.
4. The method of claim 1 wherein said basic protein is protamine sulfate.
5. The method of claim 2 wherein the concentration of poly L-lysine is between about 0.1 µM and about 1 µM.
6. The method of claim 3 wherein the concentration of poly L-ornithine is between about 0.1 µM and about 10 µM.
7. The method of claim 4 wherein the concentration of protamine sulfate is between about 10 µM and about 100 µM.
8. A method of reactivating human insulin receptor kinase, which has lost some, but not all, of its kinase activity, comprising:
    reacting human insulin receptor with poly L-lysine.
9. The method of claim 8 wherein the concentration of poly L-lysine is between about 0.1 µM and about 1 µM.
10. A method of activating kinase activity in human insulin receptor which has no insulin-sensitive kinase activity, comprising:
    reacting human insulin receptor with at poly L-lysine basic protein.
11. The method of claim 10 wherein the concentration of poly L-lysine is between about 0.1 µM and about 1 µM.

* * * * *

UNITED STATES PATENT AND TRADEMARK OFFICE
CERTIFICATE OF CORRECTION

PATENT NO. : 4,962,155

DATED : October 9, 1990

INVENTOR(S) : Yoko Fujita-Yamaguchi, Jay M. McDonald and David B. Sacks

It is certified that error appears in the above-identified patent and that said Letters Patent is hereby corrected as shown below:

Column 1, line 6, after the title insert:

--This invention was made with government support under Grant Nos. DK 29770 and DK 34427 awarded by the National Institutes of Health. The government has certain rights in the invention.--

Signed and Sealed this

Second Day of March, 1993

Attest:

STEPHEN G. KUNIN

*Attesting Officer*  *Acting Commissioner of Patents and Trademarks*